United States Patent [19]

Opitz et al.

[11] Patent Number: 4,889,690
[45] Date of Patent: Dec. 26, 1989

[54] SENSOR FOR MEASURING PHYSICAL PARAMETERS OF CONCENTRATION OF PARTICLES

[75] Inventors: Norbert Opitz, Schwerte; Dietrich W. Lübbers, Dortmund, both of Fed. Rep. of Germany

[73] Assignee: Max Planck Gesellschaft, Munich, Fed. Rep. of Germany

[21] Appl. No.: 51,252

[22] Filed: May 7, 1987

Related U.S. Application Data

[63] Continuation of Ser. No. 614,728, May 25, 1984, abandoned.

[30] Foreign Application Priority Data

May 28, 1983 [DE] Fed. Rep. of Germany ....... 3319526

[51] Int. Cl.$^4$ ..................... G01N 21/49; G02B 6/10
[52] U.S. Cl. .................... 422/73; 250/458.1; 250/461.1; 250/461.2; 250/484.1; 350/96.1; 356/336
[58] Field of Search ............ 422/73; 356/336; 250/484.1 R, 458.1, 461.1, 461.2; 350/96.1

[56] References Cited

U.S. PATENT DOCUMENTS

| | | | |
|---|---|---|---|
| 3,482,944 | 12/1969 | Plantz et al. | 422/87 |
| 3,754,867 | 8/1973 | Guenther | 436/163 |
| 3,985,505 | 10/1976 | Bredeweg | 422/68 |
| 4,003,707 | 1/1977 | Lübbers et al. | 422/68 |
| 4,071,298 | 1/1978 | Falconer | 356/336 X |
| 4,255,053 | 3/1981 | Lübbers et al. | 422/83 |
| 4,272,485 | 6/1981 | Lübbers | 422/68 |
| 4,280,815 | 7/1981 | Oberhardt et al. | 422/68 |
| 4,306,877 | 12/1981 | Lübbers et al. | 422/68 |
| 4,452,759 | 6/1984 | Takekawa | 422/73 |
| 4,548,500 | 10/1985 | Wyatt et al. | 356/336 |
| 4,557,900 | 12/1985 | Heitzmann | 422/55 |
| 4,564,598 | 1/1986 | Briggs | 422/73 X |
| 4,710,025 | 12/1987 | Wyatt et al. | 356/336 X |
| 4,717,545 | 1/1988 | Morris | 422/57 X |

OTHER PUBLICATIONS

Physil. Zeitschrift XX, 1919, Stern u. Volmer, Uber die Abklingungszeit der Fluoreszentz, pp. 183–188.
Dubois, Transfer of Electronic Energy, Quenching of Fluorescence by Oxygen and Nitric Oxide, Aeronautical Research Lab., OH, 4/23/56.
The Journal of Chemical Physics, vol. 51, No. 5, 9/1/69, pp. 2242–2246.
Data Modul, Product Brochure, 12/31/80.
Mierochimica Acta, 1984, I, "A Fast Responding Fluorescence Sensor for Oxygen", pp. 153–158.

Primary Examiner—Barry S. Richman
Assistant Examiner—Jill Johnston
Attorney, Agent, or Firm—Michael J. Striker

[57] ABSTRACT

A sensing arrangement for measuring physical parameters or concentration of particles is assembled of a laminar source of luminescent radiation. Fluorescent indicating particles are arranged in an indicator layer adjoining one major side of the laminar light source. The indicator layer adjoins a measuring space containing the object of measurement whose particles enter the indicator layer by diffusion. Fluorescent indicating particles are arranged in the indicator layer to emit fluorescent light when illuminated by the laminar light source. Photoelectric receiver is adjacent the opposite side of the laminar light source to measure the intensity of the fluorescent radiation. In a modification, luminescent phosphors and fluorescent particles are arranged in a common matrix.

25 Claims, 4 Drawing Sheets

SENSOR FOR MEASURING PHYSICAL PARAMETERS OF CONCENTRATION OF PARTICLES

This application is a continuation of application Ser. No. 614,728, filed May 25, 1984, now abandoned.

BACKGROUND OF THE INVENTION

The present invention relates in general to a device for measuring physical properties or concentration of particles and, in particular, to a sensor which includes optical indicating means arranged in an indicator layer in which the particles are dispersed, a light source and an optical indicator including at least one photoelectric receiver for measuring light emitted by the optical indicating means.

Arrangements for optical measurement of physical parameters or concentration of particles have been hitherto assembled of structural modules including an optical device for measuring light, and an indicator space containing the optical indicating means. The overall device has proven to be robust or bulky for many fields of application.

In order to use this measuring principle in new fields of application, the prior art arrangement is to be reduced in size and simultaneously the output signals should be improved.

SUMMARY OF THE INVENTION

It is, therefore, a general object of the present invention to provide an improved sensor of the above described kind which is smaller in size and improves the measuring output.

In keeping with this object and others which will become apparent hereafter, one feature of the invention resides in a sensor for measuring physical parameters or concentration of particles in the provision of a light source which is in the form of a laminar luminescent radiator.

According to this invention there can be used in principle two kinds of luminescent radiators, namely those based on electro-luminescence and on electro-chemo-luminescence.

In light sources using electro-luminescence, similarly as in light emitting diodes using p-n junctions, there are in microcrystalline ranges of a so-called phosphor semiconductors having about 1,8 electron volts band gap between the conduction band and the valence band. These semiconductors emit light quanta when electrons which have been electrically lifted in the conduction band, retransit in the valence band again. The excitation is made by alternating current via shifting currents.

In the case of an electro-chemo-luminescence by applying electrical field there are first generated chemical radicals which are then recombined and in doing so transmit light quanta. This process terminates rapidly in balance.

Inasmuch during the light emission negligible heat is generated, the radiators and photoelectric receivers can be closely packed. This has the immediate advantage that a very large spatial angle of radiation can be utilized by the photo-electric receiver and consequently the signal-noise ratio is substantially improved.

The excitation of luminescence, as mentioned before takes place either by electrical alternating fields or by static fields. The construction of a light source in the form of a lamina is of particular advantage when the photo-electric receiver is also distributed along a flat surface.

Minute, laminar devices can be produced when the indicator space, the laminar light source, optical filters and decoupling layers are applied in layers on the receiving surface of the photoelectric receiver.

A device arranged in this manner will in the following description be designated as a "physical sensor" because it enables to perform an extraordinarily large number of measuring tasks by selecting suitable indicators and phosphors whereby the overall construction remains substantially the same.

Optical filters in such physical sensors of this invention are no longer necessary provided that in the case of fluorescent indicators, the frequency range of the luminescent radiation of the source is in the frequency range of the excitation radiation of the fluorescent indicator molecules, and the fluorescent radiation of the indicator molecules corresponds to the input frequency range of the photoelectric receiver. In the case of absorption indicators, optical filters can be dispensed with when the luminescent radiation is in the input range of the photoelectric receiver.

In a further elaboration of this invention, the electroluminescent phosphor is arranged in the indicator layer. In this case the laminar luminescent surface and the indicator layer coincide.

As a consequence, a further reduction in size of the physical sensor and a further improvement of its accuracy in measuring physical parameters is obtained.

With advantage, whenever the object of measurement makes it possible, the indicators and the phosphors are sealed leakage free in a supporting matrix. In this manner the susceptibility to interference of the sensor is reduced.

This susceptibility to interference can be further reduced when the phosphors are sealed and arranged in the indicator layer or when the indicators are sealed and together with the phosphors are arranged in the laminar luminescent surface.

In a further development of this invention, the electric laminar luminescent surfaces are provided in the indicator layer. In this way, local fields of extremely high intensity can be produced especially when the electrical conductive surfaces are formed with edges or sharp tips. As a consequence, lower voltages for producing the luminescence can be applied.

For applications in which several measuring tracks for transparent objects of measurement are necessary, there are provided an indicator layer and a measuring region situated between the indicator layer and the photoelectric receiver, on either side of the laminar luminescent light source.

If it is desired to make reference measurements for checking the light intensity of the device apart from the measurement of the physical parameters or concentration of particles, a reference indicator is arranged behind or in the indicator layer.

When several measurements are to be made simultaneously in parallel in the same measuring region, then according to another feature of this invention, different phosphors emitting at different wavelengths and corresponding indicators responding to the emitted wavelength are provided in the indicator layer.

For this purpose, a linear or laminar one-piece arrays of individual sensors can be used. Alternatively, the indicators can be made by dividing in fields the photoelectric receiving surfaces, the indicator surfaces and the light emitting surfaces.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
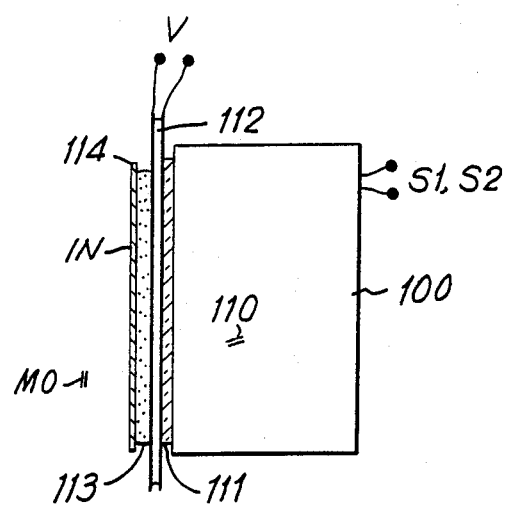
FIG. 1 shows schematically a side view of an embodiment of the sensor according to this invention.

In FIG. 1 a photoelectric receiver 110 has its input surface provided with a filtering layer 111. A laminar luminescent source 112 is arranged on the filtering layer 111 and illuminates fluorescent indicating means IN provided in an indicator layer 113. The outer surface of indicator layer 113 is coated with an optical decoupling layer 114 and is permeable to non-luminescent particles of measurement MO.

The object of measurement MO can be, for example, a sample of water whose contents of oxygen is to be measured via quenching or extinction of fluorescence of the fluorescent indicators IN whereby the measuring fluorescent light is excited by the laminar light surface 112 and measured by the photoelectric receiver 110.

Figure 2:
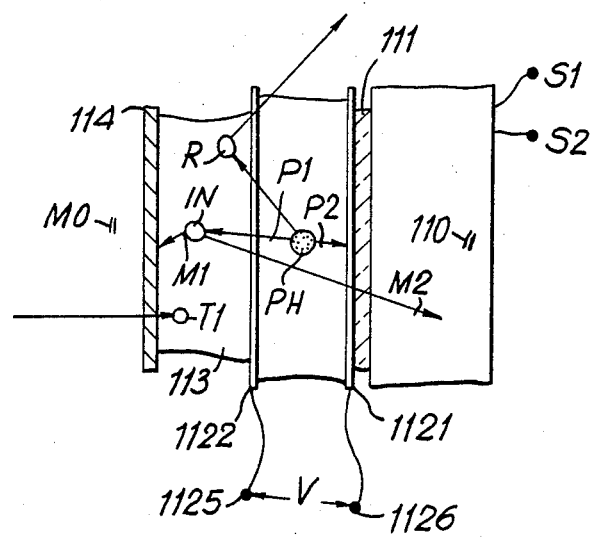
FIG. 2 is a cut-away portion of the sensor of FIG. 1, shown on an enlarged scale.

Paths of light occurring during the measuring process are illustrated by arrows in FIG. 2. The phosphor PH in this example is a chemoluminescence phosphor such as for example rubren (5,6,11-12-tetraphenyl tetraphen), dissolved in water-free BME (1,2-dimetraloxyethane). After applying an electric voltage of about 2 volts to terminals 1125 and 1126 of transparent electrodes 1121 and 1122 of the laminar luminescent light source 112, light quanta or prontons p1 and p2 are generated. The transparent electrodes are spaced apart about a distance of 50 microns. The excitation light p2 directed toward the photo-electric receiver 110 is eliminated by the filter 111 whereas the photon p1 propagates in the indicator layer 113 and excites the indicator molecules IN which emits the measuring light m1 and m2. To avoid interference, the part m1 of measuring light directed away from the photoelectric receiver, is eliminated in the decoupling layer 114 whereas the opposite part m2 of measuring light passes through the filter 111 and is detected by the photoelectric receiver 110. Magnitude of output signal at the output terminals s1 and s2 of the photoelectric receiver depends on the concentration of measured particles T1 such as oxygen, for example in the indicator layer because the particles T1 change the intensity of the emitted fluorescent light by quenching. The more particles T1 are present in the indicator layer, the smaller is the output signal at the terminals s1 and s2. Particles T1 enter the indicator chamber 113 by diffusion. Accordingly, the arrangement according to FIGS. 1 and 2 is suitable for measuring concentration of oxygen.

In order to make the measuring process independent from intensity variations, reference indicators R can be provided in the indicator layer. The reference indicators are not affected by the measured parameter, and the reference signal is measured and processed simultaneously with the measuring light, for example by creating a quotient of the reference and measuring signal.

Other particles such as ions or gas particles can be measured in a similar fashion by the selection of suitable indicators and membranes adjusted for the particles of interest. In the same manner, pressure, temperature or other physical parameters can be measured by the sensor of this invention simply by selecting corresponding indicators.

For example, in measuring partial pressure of $CO_2$ or pH value, a fluorescent indicator HPTS (hydroxypyrene sulfonic acid-trisodium salt) is combined with a phosphor of CE-doted SrS. In another example, HPTS or Perylen is combined with $T_m$ doted ZnS as phosphor to be used as a reversible fluoresence indicator for oxygen.

The sensor arrangement 100 according to FIG. 1 represents a compact "physical sensor" in which the indicators and phosphors can be changed in simple manner. This arrangement is applicable for measuring a large number of different physical parameters inclusive of concentrations of particles.

Figure 3:
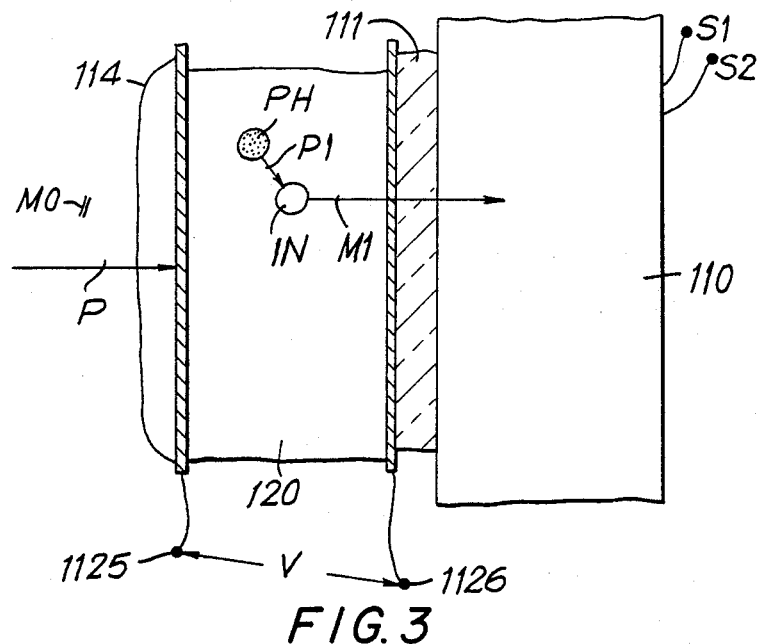
FIG. 3 is another embodiment of the sensor of this invention.

In the embodiment according to FIG. 3, phosphor molecules pH and fluorescent indicator molecules IN are embedded in a common matrix 120 such as a silicon foil. The measuring accuracy for a physical parameter P is further increased inasmuch the excitation light p1 is generated in immediate proximity to the indicator molecules IN. In the case of measuring the concentration of particles, the concentration of the measured particles in the matrix can be increased by selecting substance of the matrix which has a high coefficient of solubility for the particles. The embodiment according to FIG. 3 is simpler in structure because the light radiator and the indicator space are united.

In the arrangement where absorption indicators IN are used, the sign of the measuring light signal is reversed. In other words, if the measured parameter is more effective the measuring light is less intensive. The measuring light thus behaves as a fluorescent light which is equally influenced both by the measured physical parameter and by the concentration of particles.

The excitation voltage is applied preferably via transparent electrodes made for example of In 2.03: Sn deposited pyrolitically by spraying or vaporizing.

Figure 4:
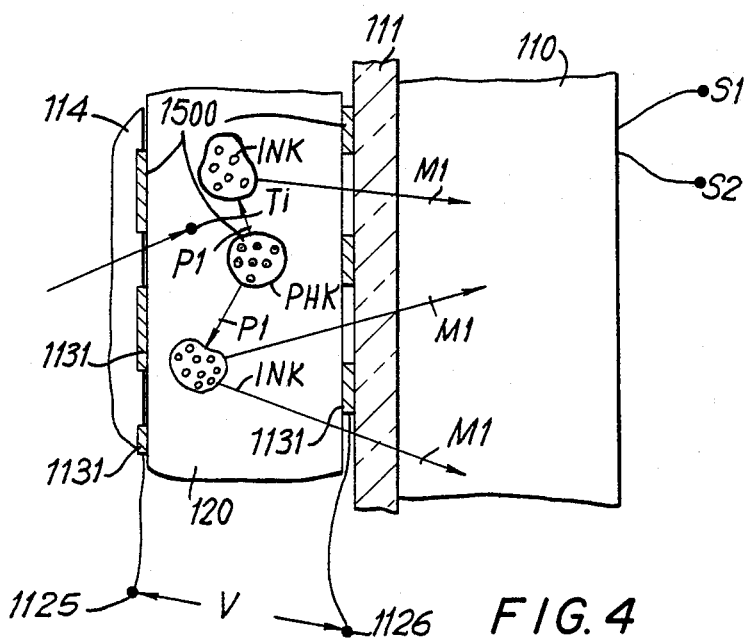
FIG. 4 is still another embodiment of the sensor of this invention.

Since the diffusion of measured particles could be offset by the excitation electrodes, a pattern of discrete electrodes 1131 according to FIG. 4 is used instead of closed electrodes. Sharp edges or tips of such conductive electrodes 1131 increase local electric field intensities and consequently lower excitation voltages are needed for perusing the luminescence.

It is of particular advantage when the supporting matrix is of a substance which permits an optimum diffusion of the measured particles. For example, when the concentration of oxygen particles is to be mesured, the matrix material must have a high permeability to $O_2$, or when the matrix material serves as an indicator layer containing optical indicating means, then for optical adjustment of the matrix material to the measured particles, the squares of solubility coefficients of the object of measurement and of the material of the indicator space are inversely proportional to the diffusion coefficients of this material. When this condition is fulfilled the interface between the matrix and the objects of measurement is optically neutralized.

In measuring diffusing particles it is advantageous when the matrix is very thin, that means in the order of microns or less because the setting time of the physical sensor is shortened and the frequency behavior is improved. For example, the matrix substance may consist of an outer layer of monomolecular lipophiler indicators.

In order to prevent tolerance problems which might result due to the interaction of indicators, phosphors and measured particles present in the same area, the phosphors and/or indicators can be embedded in microcapsules INK,PHK and indicators in still smaller nanocapsules as indicated schematically in FIG. 4. In this embodiment the indicators can be arranged in luminescent lamina or the phosphors can be arranged in the indicator layer. The indicators, phosphors and matrix are enclosed in membrane like capsules 1500. The membranes can be made of hydrophobic material, for example of lipophilic substances to protect upper surface of the matrix.

Such capsules serve also for a chemical decoupling of the sensor from the measuring space inasmuch as especially for thin matrixes in which the indicators and phosphors are immediately embedded and where phosphors and indicators situated on the upper surface are exposed to the danger of being permanently washed out, the membrane like capsules provide an additional protection.

For the case when the phosphor itself reacts to changes of measured parameters inclusive of concentration of particles with corresponding changes in luminescence intensity, then the indicators can be dispensed with.

Figure 5:
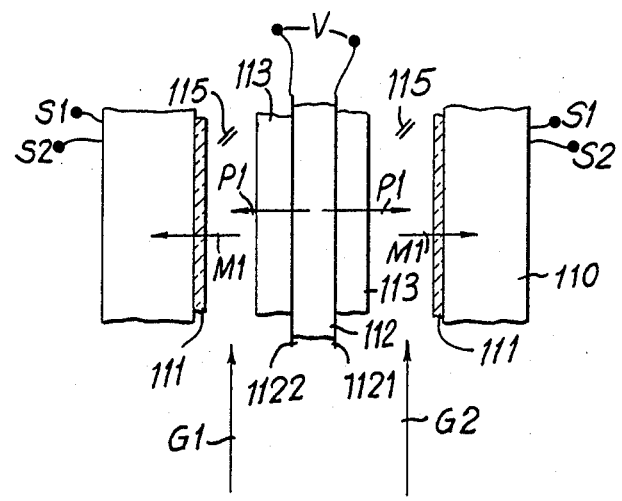
FIG. 5 is a measuring arrangement employing sensors according to this invention.

The measuring arrangement according to FIG. 5 is suitable for measuring transparent gases and liquids. The laminar light source 112 is sandwiched between two indicator layers 113 and consequently is utilized twice. The transparent objects of measurement G1 and G2 flow through measuring chambers 115 whereby the excitation light P1 radiates through the indicator layers and excites the indicators. The resulting measuring light M1 is measured by photoelectric receivers 110 at both sides of the light source 112. The effect of the object of measurement on the optical indicating means in the indicator layers 113 corresponds to the electric output signals at terminals s1 and s2 of the photoelectric receiver 110.

Figure 6:
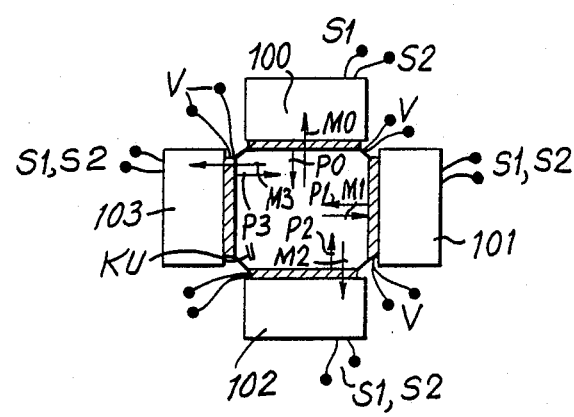
FIG. 6 is another embodiment of the measuring arrangement.

FIG. 6 illustrates an arrangement for measuring several parameters of the same object of measurement. Also in this arrangement, narrow test channels KU formed of sensors 110, 101, 102 and 103 pass through the flow of particles of measurement and are illuminated by excitation light P0, P1, P2 and P3. Measuring light M0 through M3 is measured by photo-electric receivers 100 through 103.

Figure 7:
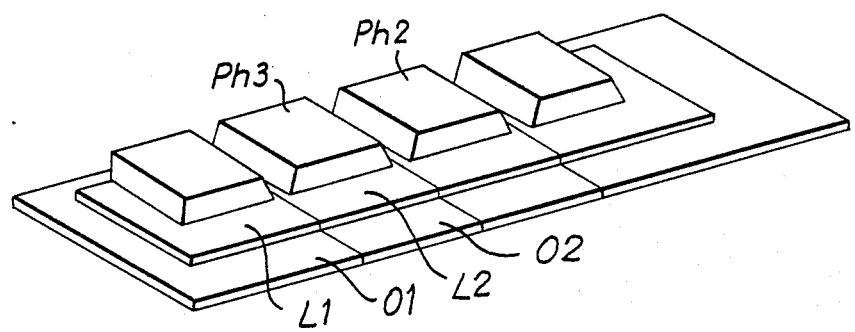
FIG. 7 is a perspective view of an array of sensors.

In a modification of this invention, the sensor has a panel like construction illustrated in FIG. 7. By means of this panel like arrangement, "spectra" of several measured parameters can be obtained. In the panel like sensor array of FIG. 7, laminar light sources L1, L2 etc. are sandwiched between discrete photoelectric receivers in the form of photo resistors PH1, PH2 etc. and panels O1, O2 etc. of indicator layers. In this example, the individual sensors are arranged in a row but it is also possible to stack the sensors into a column. The arrays of this kind are suitable for measuring flow of particles on the basis of their concentration differences or other parameters such as temperature and the like.

Figure 8:
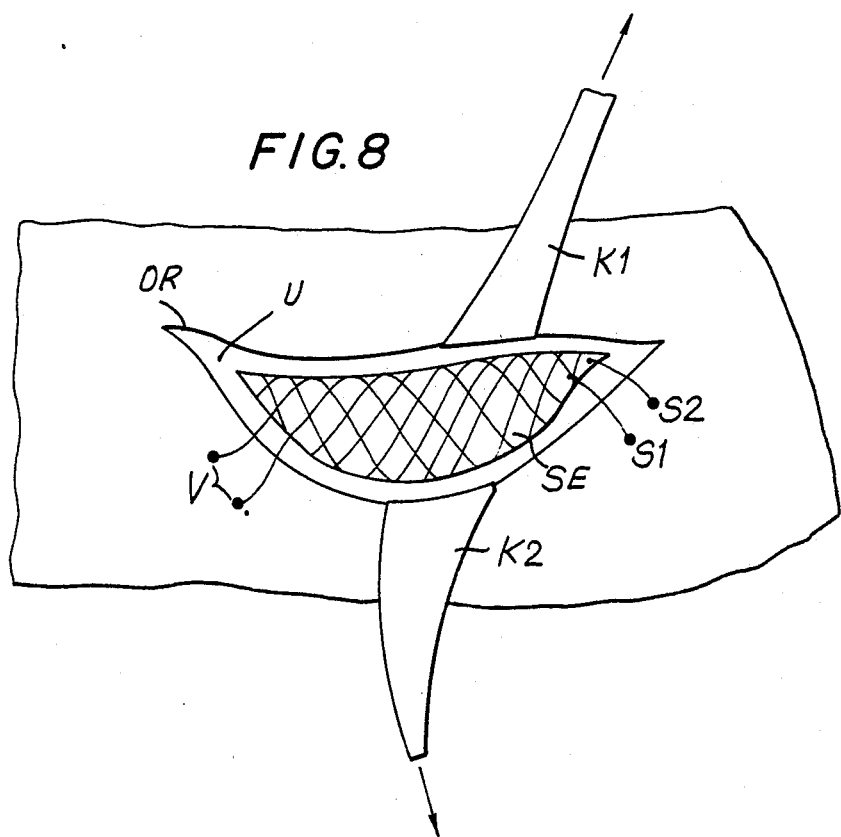
FIG. 8 is a sectional view of a sensor of this invention.

FIG. 8 illustrates a physical sensor SE with photoelectric receiver in the form of a photoelectric layer which can be easily adjusted with simple tools to the geometrical form of a field U of investigation. In this example, the sensor SE is applied on the open tissue of an organ OR whereby severed skin of the organ is held in open position by clamps K1 and K2.

It will be understood that each of the elements described above, or two or more together, may also find a useful application in other types of constructions differing from the types described above.

For instance, it is possible to equip the sensors of this invention with additional auxiliary means such as thermostats, shielding means and the like and combine the sensors with additional measuring instruments depending on the kind of measurement made.

While the invention has been illustrated and described as embodied in specific examples of the physical sensor, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A physical sensor for measuring physical parameters inclusive of concentration of particles, comprising a laminar formation assembled of a laminar source of a luminescent first radiation, an indicator layer adjoining a major side of said laminar source and being permeable to particles of measurement, said indicator layer containing molecules emitting a fluorescent second radiation when illuminated by said first radiation, fluorescence quenching of the second radiation depending on concentration of said particles of measurement dispersed in said indicator layer; and a photoelectric receiver optically coupled to said indicator layer to receive and measure said second radiation while rejecting said first radiation.

2. A sensor as defined in claim 1 wherein said photoelectric receiver faces the other major side of said laminar source.

3. A sensor as defined in claim 2, wherein the laminar light source is an electroluminescent radiator.

4. A sensor as defined in claim 2, wherein the laminar light source is electro-chemo-luminescent radiator.

5. A sensor as defined in claim 2, comprising a plurality of photoelectric receivers distributed along the other major side of the laminar light source.

6. A sensor as defined in claim 2, comprising an optical filter between the laminar light source and the photoelectric receiver to pass through the second radiation and reject the first radiation.

7. A sensor arrangement comprising a plurality of sensors according to claim 6 arranged for simultaneous measurement of different parameters of the same object of measurement.

8. A sensor as defined in claim 2, wherein the light source includes a plurality of phosphors emitting light at different wavelengths and the indicator layer including a plurality of different fluorescent molecules responsive to the different wavelengths of the phosphors.

9. A sensor as defined in claim 2, wherein the photoelectric receiver is a photoelectric resistor.

10. A sensor as defined in claim 9, wherein the the indicator layer, the laminar light source and the photoelectric resistor adjoin each other to form a laminated structure whose shape is adjustable to an area to be measured.

11. A sensor as defined in claim 2, wherein the light source includes a phosphor whose intensity of luminescence depends on the parameter to be measured.

12. A sensor as defined in claim 2, wherein the light source is separated from the indicator layer by a chemically decoupling layer and the indicator layer is separated from a measuring space by a decoupling layer permeable to particles to be measured.

13. A sensor arrangement comprising a plurality of sensors according to claim 2, assembled into a single array.

14. A sensor as defined in claim 2, wherein the outer surfaces of the indicator layer are hydrophobic.

15. A sensor as defined in claim 1, wherein the absorption range of the fluorescent molecules and the second radiation correspond to the sensitivity range of the photoelectric receiver.

16. A sensor as defined in claim 1, further comprising at least one fluorescent reference molecule arranged in the indicator layer.

17. A sensor as defined in claim 1, comprising means for regulating additional physical parameters of the object of measurement.

18. A sensor as defined in claim 1, wherein the indicator layer is made as a matrix including a solvent substance for the particles of measurement, the squares of dissolution coefficients of the particles of measurement and of the indicator particles in the solvent substance being substantially inversely proportional to the diffusion coefficients of the particles of measurement and of the indicator particles in the matrix.

19. A physical sensor for measuring physical parameters inclusive of concentration of particles, comprising a laminar light source in the form of a laminar matrix containing phosphor particles emitting a luminescent first radiation when energized and molecules emitting a fluorescent radiation when exposed to said first radiation, said matrix being permeable to said particles of measurement, fluorescence quenching of said second radiation depending on concentration of said particles of measurement dispersed in said matrix; and a photoelectric receiver optically coupled to said fluorescent molecules to receive and measure said second radiation while rejecting said first radiation.

20. A sensor as defined in claim 19 wherein said phosphor particles are sealed in a plurality of capsules arranged in said matrix.

21. A sensor as defined in claim 10 wherein said fluorescent molecules are sealed in a plurality of capsules arranged in said matrix.

22. A sensor as defined in claim 19, comprising electrical electrodes arranged at opposite sides of the matrix to energize the phosphor particles.

23. A sensor as defined in claim 22 wherein the electrical electrodes on each side of the matrix are separated and provided with sharp tips to increase local electric field intensities.

24. A sensor as defined in claim 22, wherein the electrical electrodes on each side of the matrix are separated and provided with edges.

25. A sensor arrangement for measuring physical parameters inclusive of concentration of particles, comprising a laminar source of a luminescent first radiation when energized; two indicator layers adjoining opposite major sides of said laminar source and each containing molecules emitting a fluorescent second radiation when exposed to said first radiation, two photoelectric receivers each facing an assigned indicator layer; and gaps resulting between respective indicator layers and photoelectric receivers receiving said particles of measurement.

* * * * *